United States Patent
Khachik et al.

(10) Patent No.: US 8,222,458 B2
(45) Date of Patent: Jul. 17, 2012

(54) PROCESS OR SYNTHESIS OF (3S)- AND (3R)-3-HYDROXY-BETA-IONONE, AND THEIR TRANSFORMATION TO ZEAXANTHIN AND BETA-CRYPTOXANTHIN

(75) Inventors: Frederick Khachik, Rockville, MD (US); An-Ni Chang, Greenbelt, MD (US)

(73) Assignee: University of Maryland, College Park, College Park, MD (US)

( * ) Notice: Subject to any disclaimer, the term of this patent is extended or adjusted under 35 U.S.C. 154(b) by 456 days.

(21) Appl. No.: 12/484,703

(22) Filed: Jun. 15, 2009

(65) Prior Publication Data

US 2009/0311761 A1    Dec. 17, 2009

Related U.S. Application Data

(60) Provisional application No. 61/061,355, filed on Jun. 13, 2008.

(51) Int. Cl.
*C07C 45/67* (2006.01)
*C12P 7/26* (2006.01)

(52) U.S. Cl. ........................ 568/341; 435/148
(58) Field of Classification Search .................. 568/341; 435/148
See application file for complete search history.

(56) References Cited

U.S. PATENT DOCUMENTS

| 3,471,569 A | 10/1969 | Freyschlag et al. |
| 6,274,772 B1 * | 8/2001 | Teissier et al. ................ 568/341 |
| 2009/0238933 A1 | 9/2009 | Khachik |
| 2009/0264681 A1 | 10/2009 | Khachik et al. |

FOREIGN PATENT DOCUMENTS

| DE | 1 031 301 | 6/1958 |
| DE | 1 216 862 | 5/1966 |

OTHER PUBLICATIONS

Broom, S.J., et al., "Synthesis of (±)-*E*-4-(1,2,4-Trihydroxy-2,6,6-trimethylcyclohexyl)-but-en-2-one: A Novel Degraded Cartenoid Isolated from New Zealand Thyme (*Thymus vulgaris*) Honey," *Tetrahedron Letters*, 33: 3197-3200 (1992), Pergamon Press Ltd., Great Britain, UK.

Campbell, A.N., et al., "The Acetone—Acetic Anhydride—Carbon Disulfide System: Surface Tension, Viscosity, and Total and Partial Vapor Pressures," *Canadian Journal of Chemistry, 49*: 2368-2371 (1971), The National Research Council of Canada, Ontario, Canada.

English language Abstract for DE 1 216 862 (listed as document FP2 on the accompanying form PTO/SB/08A), May 18, 1966.

Isler, O., et al., "55. Synthesen in der Carotinoid-Reihe. Totalsynthese von Kryptoxanthin und eine weitere Synthese von Zeaxanthin," *Helvetica Chimica Acta, XL*:456-467(1957), Verlag Helvetica Chimica Acta, Zürich, Switzerland.

Loeber, D., et al., "Carotenoids and Related Compounds. Part XXVIII. Synthesis of Zeaxanthin, β-Cryptoxanthin, and Zeinoxanthin (α-Cryptoxanthin)," *J. Chem. Soc., C*: 404-408 (1971), Royal Society of Chemistry, London, UK.

Marwah, P., et al., "An economical and green approach for the oxidation of olefins to enones," *Green Chemistry*, 6: 570-577(2004), Royal Society of Chemistry, London, UK.

Rüttimann, A.V. and Mayer, H., "154. Synthese von optisch aktiven, natürlichen Carotinoiden and strukturell verwandten Naturprodukten V. Synthese von (3R,3'R)-, (3S,3'S)- und (3R,3'S; meso)-Zeaxanthin durch asymmetrische Hydroborierung. Ein neuer Zugang zu optisch aktiven Carotinoidbausteinen," *Helvetica Chimica Acta*, 63:1456-1462 (1980), Verlag Helvetica Chimica Acta, Zürich, Switzerland.

Soukup, M., et al., "88. Technical Procedures for the Syntheses of Carotenoids and Related Compounds from 6-Oxo-isophorone: Syntheses of (3R,3'R)-Zeaxanthin," *Helvetica Chimica Acta*, 73:868-873 (1990), Verlag Helvetica Chimica Acta, Zürich, Switzerland.

Widmer, E., et al.,"87. Technical Procedures for the Syntheses of Carotenoids and Related Compounds from 6-Oxo-isophorone: Syntheses of (3R,3'R)-Zeaxanthin," *Helvetica Chimica Acta*, 73:861-867 (1990), Verlag Helvetica Chimica Acta, Zürich, Switzerland.

Yang, M., et al., "$CaCl_2$- or $MgCl_2$-Catalyzed Allylic Oxidations of Ionone-like Dienes," *Synlett*, 16: 2617-2620 (2006), Thieme, New York, NY, U.S.A.

* cited by examiner

*Primary Examiner* — Sikarl Witherspoon
(74) *Attorney, Agent, or Firm* — Sterne, Kessler, Goldstein & Fox P.L.L.C.

(57) ABSTRACT

Disclosed is a process for the synthesis of (3R)-3-hydroxy-β-ionone and its (3S)-enantiomer in high optical purity from commercially available (rac)-α-ionone. The key intermediate for the synthesis of these hydroxyionones is 3-keto-α-ionone ketal that was prepared from (rac)-α-ionone after protection of this ketone as a 1,3-dioxolane. Reduction of 3-keto-α-ionone ketal followed by deprotection, lead to 3-hydroxy-α-ionone that was transformed into (rac)-3-hydrox-β-ionone by base-catalyzed double bond isomerization in 46% overall yield from (rac)-α-ionone. The racemic mixture of these hydroxyionones was then resolved by enzyme-mediated acylation in 96% ee. (3R)-3-Hydroxy-β-ionone and its (3S)-enantiomer were respectively transformed to (3R)-3-hydroxy-(β-ionylideneethyl)triphenylphosphonium chloride [(3R)-$C_{15}$-Wittig salt] and its (3S)-enantiomer [(3S)-$C_{15}$-Wittig salt] according to known procedures. Double Wittig condensation of these Wittig salts with commercial available 2,5- dimethtylocta-2,4,6-triene-1,8-dial provided all 3 stereoisomers of zeaxanthin. Similarly, (3R)-$C_{15}$-Wittig and its (3S)-enantiomer were each coupled with β-apo-12'-carotenal.

20 Claims, No Drawings

PROCESS OR SYNTHESIS OF (3S)- AND (3R)-3-HYDROXY-BETA-IONONE, AND THEIR TRANSFORMATION TO ZEAXANTHIN AND BETA-CRYPTOXANTHIN

BACKGROUND OF THE INVENTION

1. Field of the Invention

The invention is in the field of organic chemistry. The invention relates to a process for the synthesis of (3R)-3-hydroxy-β-ionone and (3S)-3-hydroxy-β-ionone in high enantiomeric purity from commercially available (rac)-α-ionone. These ionones have been transformed into (3R,3'R)-zeaxanthin, (3S,3'S)-zeaxanthin, (3R,3'S;meso)-zeaxanthin, (3R)-β-cryptoxanthin, and (3S)-β-cryptoxanthin by a $C_{15}$+$C_{10}$+$C_{15}$ coupling strategy according to known procedures.

2. Background Art (3R)-3-Hydroxy-β-ionone and (3S)-3-hydroxy-β-ionone are two important intermediates in the synthesis of carotenoids with β-end group such as lutein, zeaxanthin, β-cryptoxanthin, and their stereoisomers. However, among the various stereoisomers of these carotenoids, only (3R,3'R,6'R)-lutein, (3R,3'R)-zeaxanthin, and (3R)-β-cryptoxanthin are present in most fruits and vegetables commonly consumed in the US. These carotenoids accumulate in the human plasma and major organs and exhibit antioxidant and anti-inflammatory properties that are important biological functions in protection against chronic diseases. (3R,3'R,6'R)-Lutein and (3R,3'R)-zeaxanthin also accumulate in the human ocular tissues [macula, retinal pigment epithelium (RPE), ciliary body, iris, lens] and have been implicated in the prevention of age-related macular degeneration (AMD). (3R)-β-Cryptoxanthin is also present in selected ocular tissues at a very low concentration whereas (3R,3'S;meso)-zeaxanthin which is absent in foods and human plasma is present in nearly all tissues of the human eye in relatively high levels. The biological activity of the other non-dietary stereoisomers of these carotenoids is not known at present. The structures of all possible stereoisomers of zeaxanthin (1-3) and β-cryptoxanthin (4 and 5) are shown in Scheme 1.

Scheme 1. The Chemical structures of zeaxanthin, β-cryptoxanthin, and their stereoisomers.

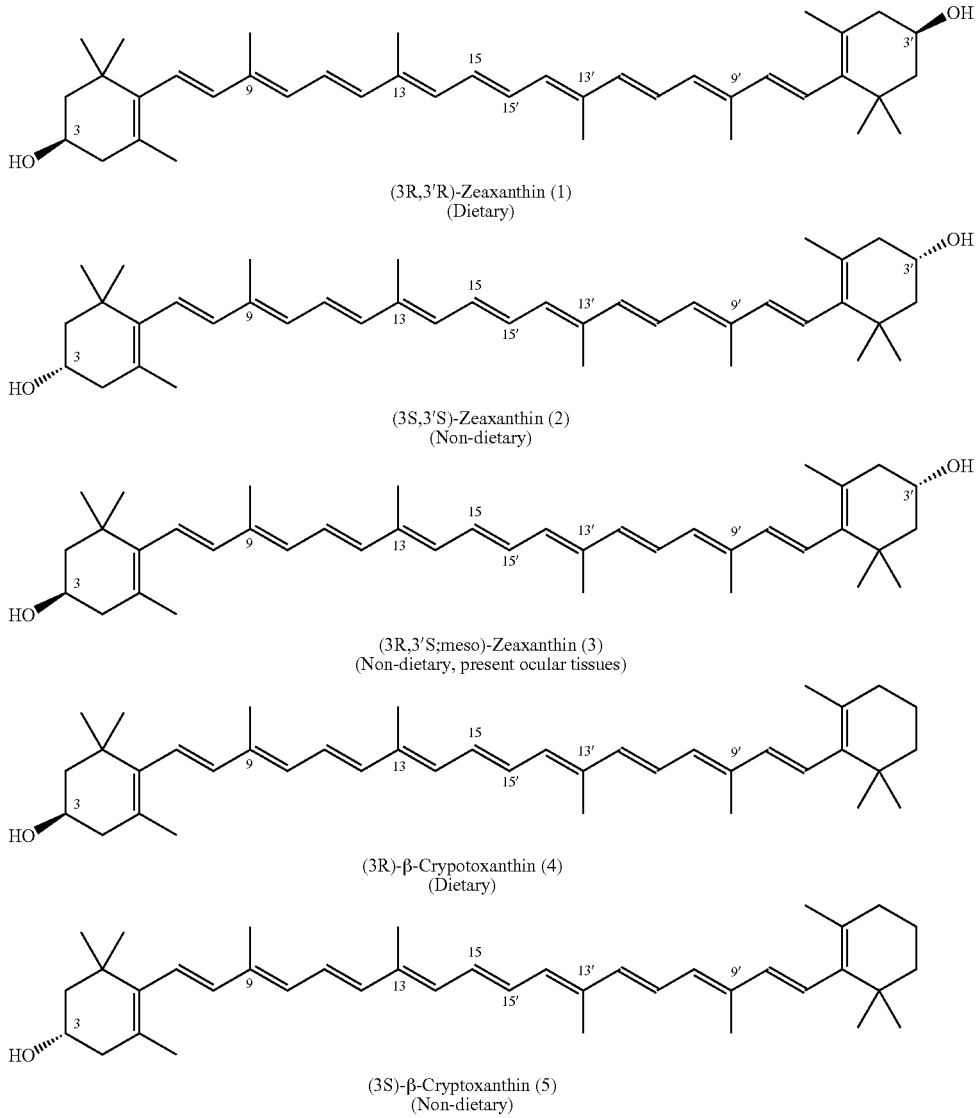

(3R,3'R)-Zeaxanthin (1)
(Dietary)

(3S,3'S)-Zeaxanthin (2)
(Non-dietary)

(3R,3'S;meso)-Zeaxanthin (3)
(Non-dietary, present ocular tissues)

(3R)-β-Crypotoxanthin (4)
(Dietary)

(3S)-β-Cryptoxanthin (5)
(Non-dietary)

The first total synthesis of optically inactive (rac)-zeaxanthin and (rac)-β-cryptoxanthin was first reported in 1957 by Isler et al. (*Helv. Chim. Acta,* 1957, 40:456-467) employing $C_{19}$+$C_2$+$C_{19}$ and $C_{19}$+$C_{21}$ Wittig coupling strategies, respectively. However, a more practical total synthesis of these carotenoids was developed by Loeber et al. [*J. Chem. Soc (C)*, 1971, 404-408] by implementing a $C_{15}$+$C_{10}$+$C_{15}$ double Wittig reaction for synthesis of (rac)-zeaxanthin and a $C_{25}$+$C_{15}$ Wittig coupling reaction for the synthesis of (rac)-β-cryptoxanthin as shown in Scheme 2.

Scheme 2. The total synthesis of (rac)-zeaxanthin and (rac)-β-cryptoxanthin according to the method of Loeber et al. [*J. Chem. Soc* (C), 1971, 404-408].

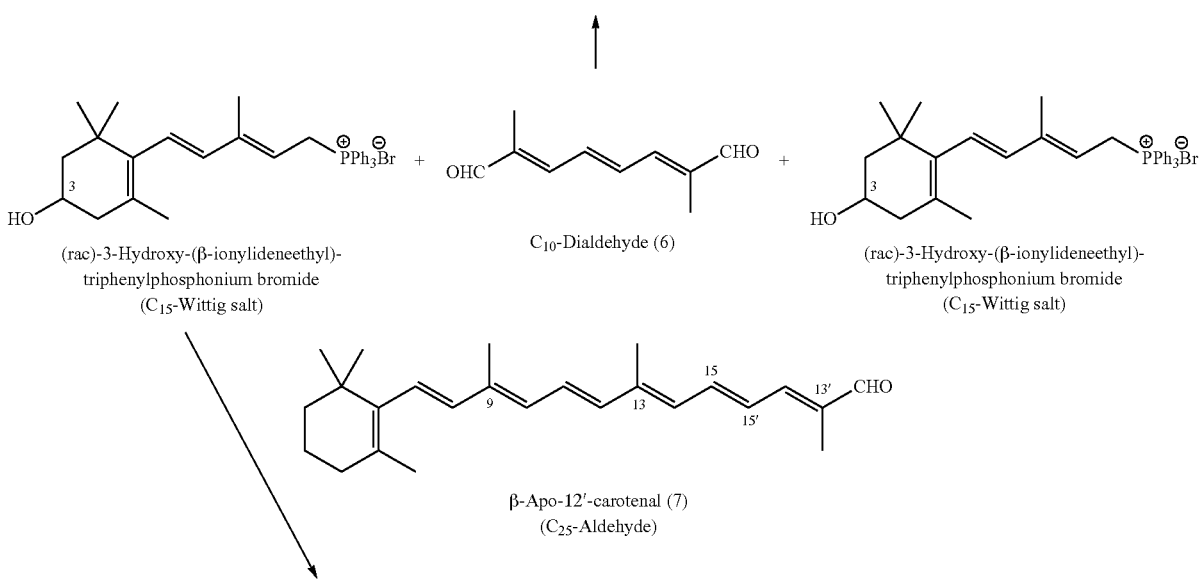

According to this procedure, the key intermediates for the synthesis of (rac)-zeaxanthin was (rac)-3-hydroxy-(β-ionylideneethyl)triphenylphosphonium bromide that was coupled with the commercially available C$_{10}$-dialdehyde 6 in a double Wittig reaction to yield a racemic mixture of 1-3 (Scheme 2). Similarly, (rac)-β-cryptoxanthin (4+5) was prepared by the Wittig condensation of the readily accessible β-apo-12'-carotenal (7) with (rac)-3-hydroxy-(β-ionylideneethyl)triphenylphosphonium bromide (C$_{15}$-Wittig salt). This C$_{15}$-Wittig salt was prepared in 8 steps from 4-ethylenedioxy-2,2,6-trimethylcyclohexanone that was sequentially converted to (rac)-3-hydroxy-β-ionone [mixture of (3R): 8 and (3S): 9] and 3-hydroxy-vinyl-α-ionol [mixture of (3R): 10 and (3S): 11] (Scheme 3).

Scheme 3. Synthesis of (rac)-3-hydroxy-(β-ionylideneethyl)triphenylphosphonium bromide (C$_{15}$-Wittig salt) according to the method of Loeber et al. [*J. Chem. Soc* (C), 1971, 404-408].

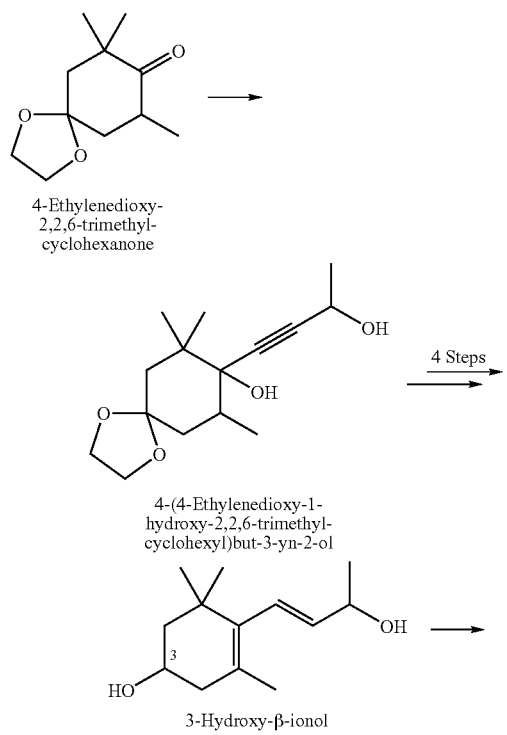

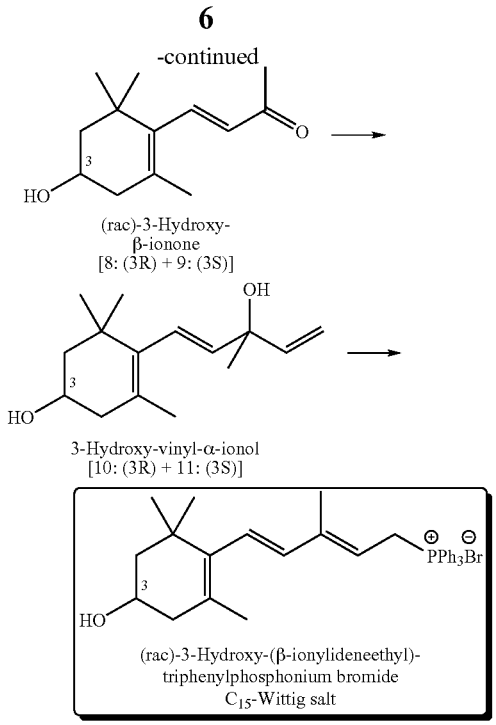

The first total synthesis of optically active (3R)-3-hydroxy-(β-ionylideneethyl)-triphenylphosphonium chloride (12) and its (3S)-isomer (13) was reported in 1980 by Rüttimann and Mayer (*Helv. Chim. Acta*, 1980, 63:1456-62) according to Scheme 4. The key starting materials in this synthesis were (3R)-3-hydroxy-β-cyclogeranial and (3S)-3-hydroxy-β-cyclogeranial that were each prepared in 5 steps from 2,6,6-trimethyl-1,3-cyclohexadiene-1-carboxaldehyde (Safranal). These aldehydes were then converted to (3R)-3-hydroxy-β-ionone (8) and (3S)-3-hydroxy-β-ionone (9). In the following steps, the method of Loeber et al. [*J. Chem. Soc* (C), 1971, 404-408] was employed to transform these hydroxyionones into (3R)-3-hydroxy-(β-ionylideneethyl)triphenylphosphonium chloride (12) and its (3S)-isomer (13). However, the major difference was that the optically active (3R)-3-Hydroxy-β-ionone (8) and (3S)-3-hydroxy-β-ionone (9) were separately converted to (3R)-3-hydroxy-vinyl-α-ionols (10) and its (3S)-isomer (11), respectively. The optically active Wittig salts 12 and 13, prepared from these ionol, were then transformed into (3R,3'R)-, (3S,3'S)-, and (3R,3'S;meso)-zeaxanthin in double Wittig reactions with C$_{10}$-dialdehyde 6 similar to the method of Loeber et al. shown in Scheme 2.

Scheme 4. Synthesis of (3R)-3-hydroxy-(β-ionylideneethyl)triphenylphosphonium chloride and its (3S)-isomer reported by Rüttimann and Mayer (*Helv. Chim. Acta*, 1980, 63:1456-62).

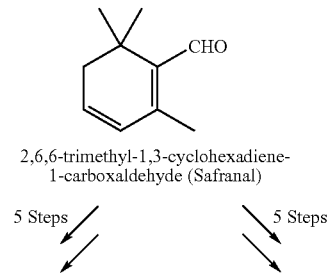

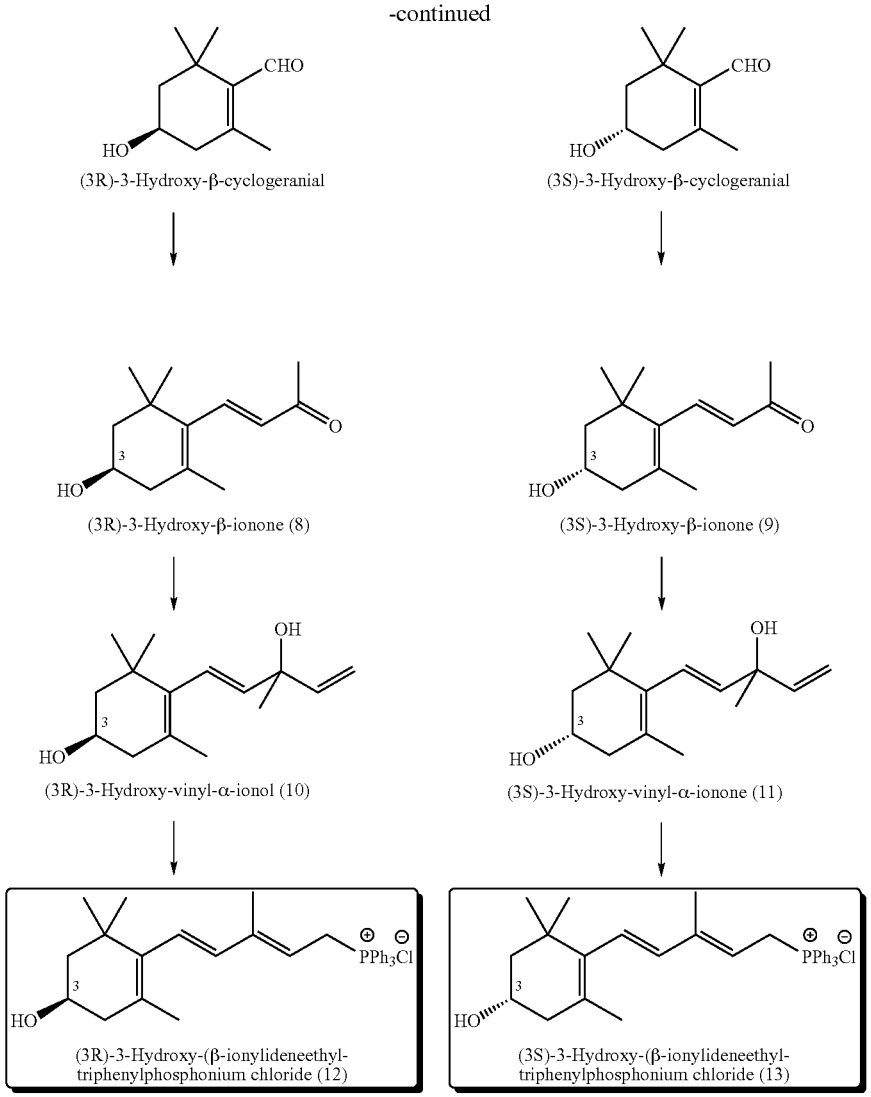

Two additional processes for the technical synthesis of (3R, 3'R)-zeaxanthin via Wittig salt 12 were also developed a decade later by Widmer et al. (*Helv. Chim. Acta,* 1990, 73:861-67) and Soukup et al. (*Helv. Chim. Acta,* 1990, 73:868-873). These processes did not involve 3-hydroxy-β-ionone as an intermediate and in both cases employed 4-hydroxy-2,2,6-trimethylcyclohexanone as the key starting material.

In summary, since 1971 numerous reports have clearly demonstrated that the synthesis of (rac)-zeaxanthin and its three stereoisomers can be readily accomplished from the Wittig reaction of the racemic or optically active $C_{15}$-Wittig salt (12 and/or 13) with $C_{10}$-dialdehyde 6 by a $C_{15}+C_{10}+C_{15}$ coupling strategy. Furthermore, in the synthetic strategies developed by Loeber et al. [*J. Chem. Soc (C)*, 1971, 404-408] as well as Rüttimann and Mayer (*Helv. Chim. Acta,* 1980, 63:1456-62), 3-hydroxy-β-ionone has been shown to serve as the key starting material for the total synthesis of zeaxanthin. However, the synthesis of optically active (3R)-3-hydroxy-β-ionone and its (3S)-isomer by a relatively straightforward process is lacking and the development of such a process can considerably simplify the total synthesis of zeaxanthin, β-cryptoxanthin, and their stereoisomers. Therefore, the present invention was developed to provide a more practical route to 8 and 9 by employing a divergent synthetic strategy that could be applied to the synthesis of Wittig salts 12 and 13. These Wittig salts have been utilized in the synthesis of (3R, 3'R)-zeaxanthin, (3S,3'S)-zeaxanthin, (3R,3'S;meso)-zeaxanthin, (3R)-β-cryptoxanthin, and (3S)-β-cryptoxanthin.

BRIEF SUMMARY OF THE INVENTION

The retrosynthetic pathways employed in the present invention is shown in Scheme 5. In contrast to the previous reported synthesis, we rationalized that the optically active (3R)-3-hydroxy-β-ionone (8) and its (3S)-enantiomer (9) can be separated by enzyme-mediated acylation of the racemic mixture via (3R)-3-acetoxy-β-ionone (14). (rac)-3-Hydroxy-β-ionone could be prepared from (rac)-3-hydroxy-α-ionone (15) by base-catalyzed double bond isomerization. Hydroxy-ionone 15 could in turn be prepared in 4 convenient steps from the commercially available and inexpensive (rac)-α-ionone via 3-hydroxy-α-ionone ketal 16, 3-keto-α-ionone ketal 17, and α-ionone ketal 18.

Scheme 5. Retrosynthesis of (3S)- and (3R)-3-hydroxy-β-ionone from (rac)-α-ionone.*

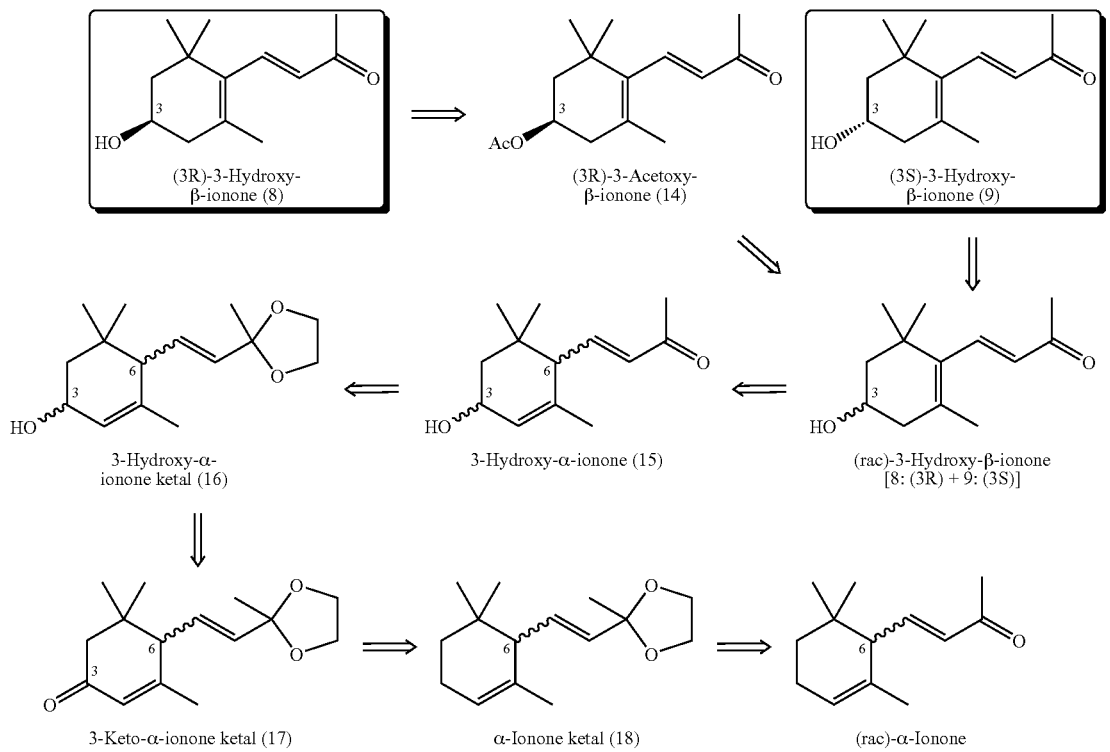

*Carotenoid numbering system has been used for all precursors of 3-hydroxy-β-ionone.

Therefore as shown in Scheme 6, carbonyl group of (rac)-α-ionone was first protected by ethylene glycol to yield α-ionone ketal 18 in nearly quantitative yield. This ketal was then oxidized in the allylic position with tert-BuOOH (TBHP, 70% in water), household bleach, and catalytic amounts of $K_2CO_3$ in acetonitrile at −5 to 0° C. to afford 3-keto-α-ionone ketal 17 in 83% yield from (rac)-α-ionone.

Scheme 6. Synthesis of 3-keto-α-ionone ketal (17) from (rac)-α-ionone.*

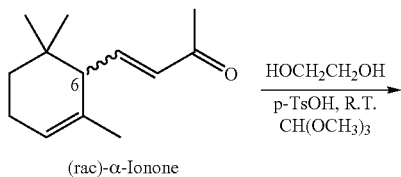

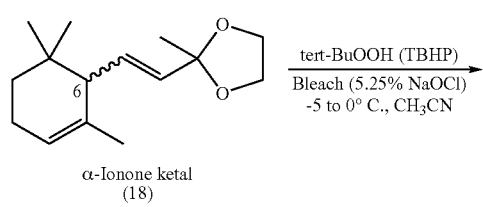

-continued

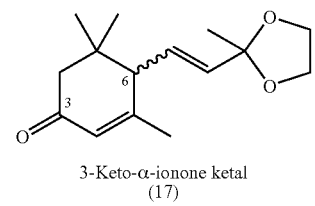

3-Keto-α-ionone ketal (17)

*Carotenoid numbering system has been used.

The transformation of 3-keto-α-ionone ketal 17 to (rac)-3-hydroxy-β-ionone (8+9) is shown in Scheme 7. The reduction of 3-keto-α-ionone ketal 17 with a number of reducing agents was investigated to determine whether the carbonyl group in this compound could be reduced stereoselectively at C3 relative to C6 position. However, no significant stereoselectivity with various reagents could be achieved. Among the reducing agents employed, potassium tri-sec-butylborohydride (K-SELECTRIDE™) at −30° C. in TBME or THF produced the highest yield (85%) of 3-hydroxy-α-ionone ketal 16. As part of the work-up of this reaction, ketal 16 was deprotected to 3-hydroxy-α-ionone (15) in dilute HCl at ambient temperature. Double bond isomerization of hydroxyionone 15 to (rac)-3-hydroxy-β-ionone (8+9) was accomplished by base catalyzed isomerization with KOH/MeOH (10%, wt/v) in 65% isolated yield after purification by column chromatography. Up to this point, the overall yield of (rac)-3-hydroxy-β-ionone from (rac)-α-ionone based on the pathways shown in Schemes 6 and 7 was 46%.

Scheme 7. Synthesis of (rac)-3-hydroxy-β-ionone from 3-keto-α-ionone ketal 17.*

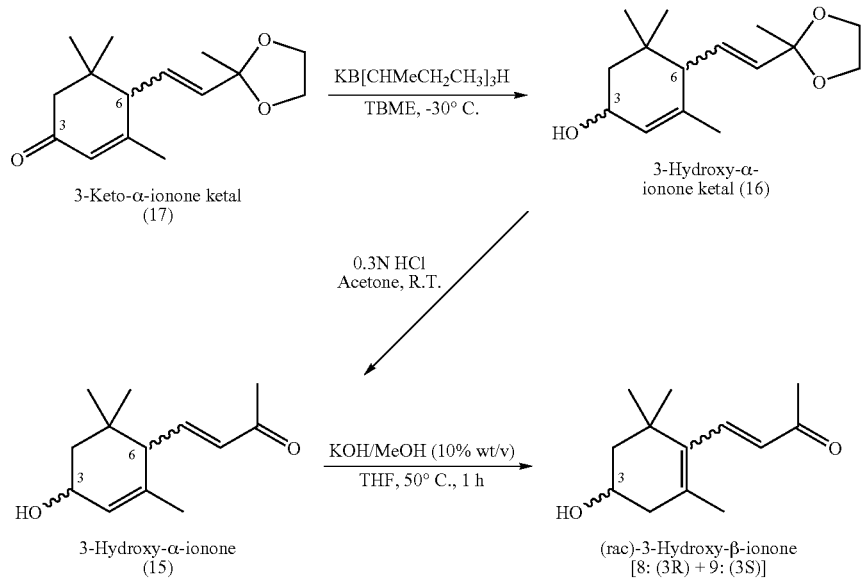

*Caroteniod numbering system has been used.

(rac)-3-Hydroxy-β-ionone (8+9) was then subjected to enzyme-mediated acylation with lipase PS (*pseudomonas cepacia*) in the presence of vinyl acetate to yield a mixture of (3R)-3-acetoxy-β-ionone (14) and (3S)-3-hydroxy-β-ionone (9) as shown in Scheme 8. After separation of ionones 9 and 14 by column chromatography and hydrolysis of the latter, (3R)-3-hydroxy-β-ionone and its (3S)-isomer were each obtained in 96% enantiomeric excess (ee).

Scheme 8. Separation of (3R)-3-hydroxy-β-ionone (8) from its 3S-isomer (9) by enzyme-mediated acylation.*

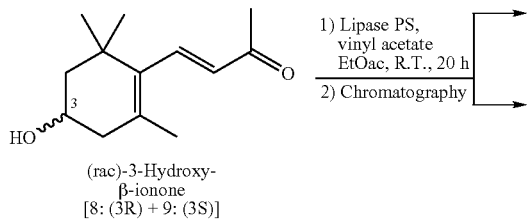

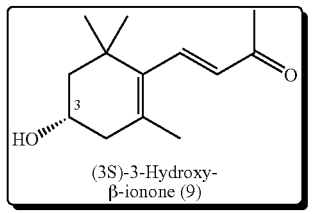

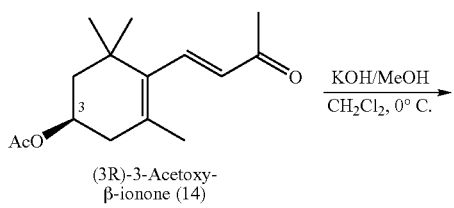

-continued

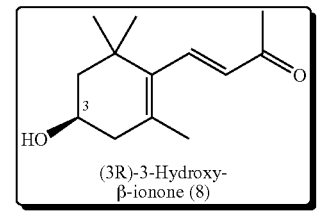

*Carotenoid numbering system has been used.

In the following steps, ionones 8 and 9 were separately converted to the Wittig salts 12 and 13, respectively via vinyl-α-ionols 10 and 11 according to the reported procedure by Rüttimann and Mayer (*Helv. Chim. Acta,* 1980, 63:1456-62) (Scheme 9).

Scheme 9. Transformation of (3R)-3-hydroxy-β-ionone (8) and its 3S-isomer (9) to Wittig salts 12 and 13 according to published procedures.*

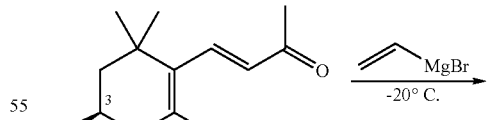

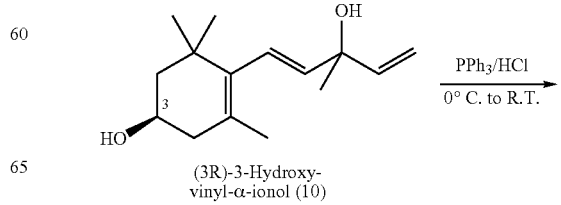

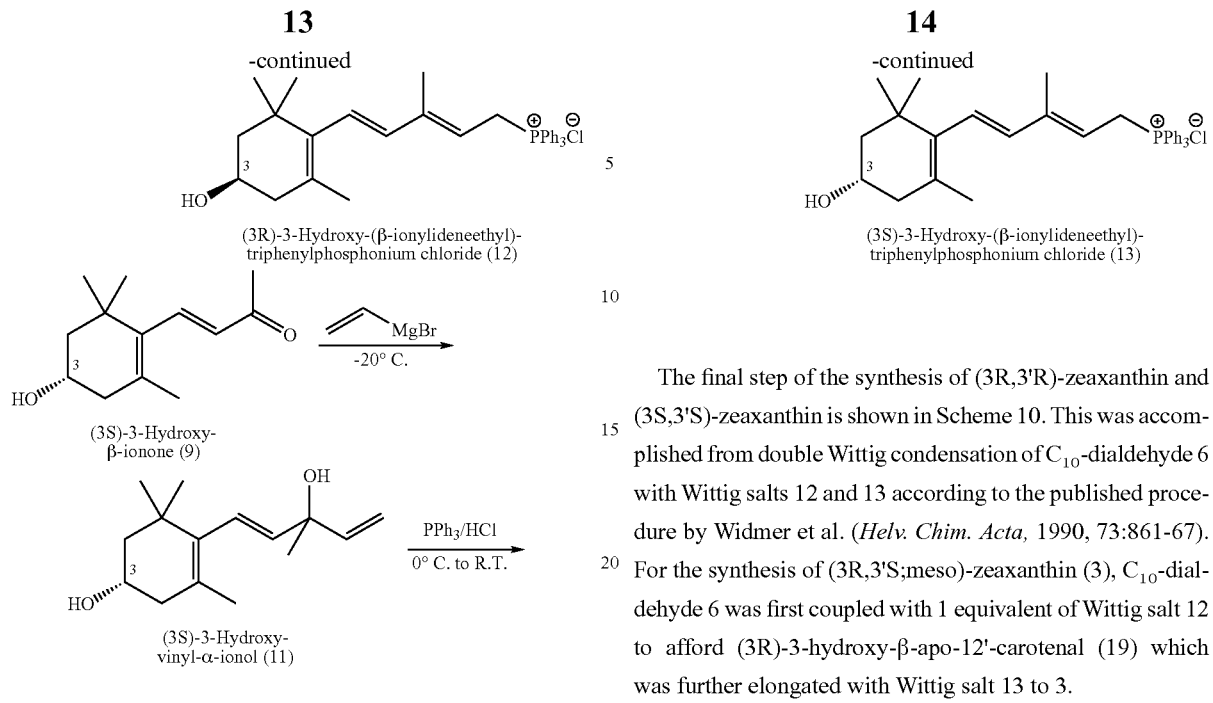

The final step of the synthesis of (3R,3'R)-zeaxanthin and (3S,3'S)-zeaxanthin is shown in Scheme 10. This was accomplished from double Wittig condensation of $C_{10}$-dialdehyde 6 with Wittig salts 12 and 13 according to the published procedure by Widmer et al. (*Helv. Chim. Acta,* 1990, 73:861-67). For the synthesis of (3R,3'S;meso)-zeaxanthin (3), $C_{10}$-dialdehyde 6 was first coupled with 1 equivalent of Wittig salt 12 to afford (3R)-3-hydroxy-β-apo-12'-carotenal (19) which was further elongated with Wittig salt 13 to 3.

Scheme 10. Synthesis of (3R,3'R)-, (3S,3'S)-, and (3R,3'S;meso)-zeaxanthin from Wittig salts 12 and 13.

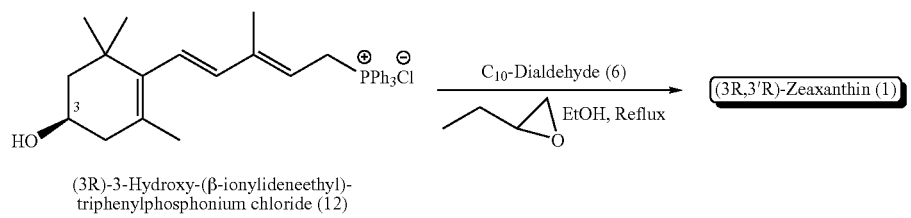

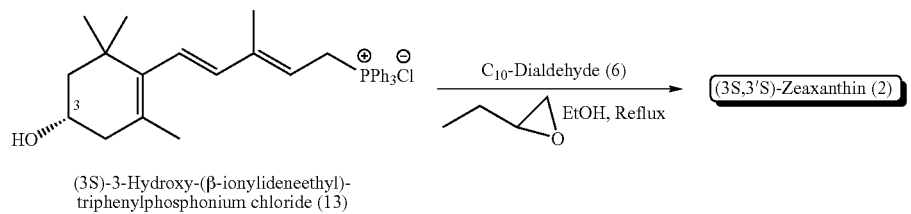

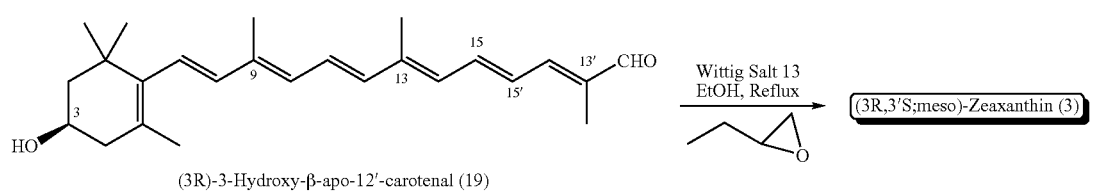

(3R)-β-Cryptoxanthin and its (3S)-enantiomer were prepared from condensation of β-apo-12'-carotenal (20) with Wittig salts 12 and 13, respectively (Scheme 11). β-Apo-12'-carotenal (20) was prepared according to the known methods (Freyschlag et al. S. Afri. Patents 66/5814 and 67/1684, 1967).

β-ionone (14) while (3S)-3-hydroxy-β-ionone (9) remains unesterified. In some embodiments, the lipase is immobilized. In some embodiments, the acyl donor is vinyl acetate, vinyl benzoate, or isopropenyl acetate. In some embodiments, (3R)-3-acetoxy-β-ionone (14) and (3S)-3-hydroxy-β-ionone (9) are separated, e.g. via column chromatography Scheme 11.Synthesis of (3R)-β-cryptoxanthin and its (3S)-enantiomer from β-apo-12'-carotenal and Wittig salts 12 and 13.

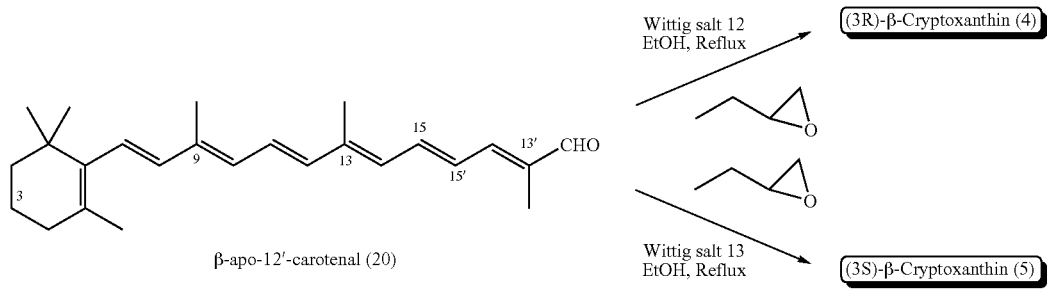

In one embodiment of the present invention, a compound having the Formula I:

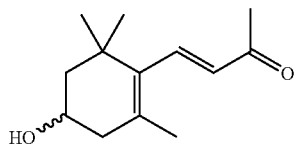

is prepared by isomerizing a compound having the Formula II:

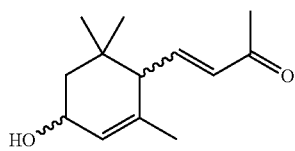

to obtain a compound having the Formula I. In some embodiments, a compound having the Formula I is prepared from a compound having the Formula II by base-catalyzed double isomerization by reacting the compound having the Formula II with a mineral base or an organic base at a temperature ranging from 45° C. to 60° C. In some embodiments, the mineral base is sodium hydroxide (NaOH) or potassium hydroxide (KOH).

In some embodiments, the compound having the Formula I is a racemic mixture of (rac)-3-hydroxy-β-ionone. In some embodiments, the compound having the Formula I is a racemic mixture of (3R)-3-hydroxy-β-ionone (8) and (3S)-3-hydroxy-β-ionone (9). In some embodiments, a racemic mixture of (3R)-3-hydroxy-β-ionone (8) and (3S)-3-hydroxy-β-ionone (9) is stereoselectively acylated using enzyme-mediated stereoselective acylation, and (3R)-3-acetoxy-β-ionone (14) is separated from unesterified (3S)-3-hydroxy-β-ionone (9) using column chromatography.

In some embodiments, a racemic mixture of (3R)-3-hydroxy-β-ionone (8) and (3S)-3-hydroxy-β-ionone (9) is acylated with lipase PS (*Pseudomonas cepacia*) or lipase AK (*Pseudomonas fluorescens*) in the presence of an acyl donor to convert (3R)-3-hydroxy-β-ionone (8) to (3R)-3-acetoxyusing n-silica. In some embodiments, the chromatography column is eluted with a combination of (1) at least one hydrocarbon solvent selected from the group consisting of pentane, hexane, heptane and cyclohexane, and (2) ethyl acetate or acetone.

In some embodiments, (3R)-3-acetoxy-β-ionone (14) is saponified with, e.g. alcoholic potassium hydroxide (KOH) or sodium hydroxide (NaOH) to obtain (3R)-3-hydroxy-β-ionone (8).

In some embodiments, (3R,3'R)-zeaxanthin (1), (3S,3'S)-zeaxanthin (2), (3R,3'S;meso)-zeaxanthin (3), (3R)-β-cryptoxanthin (4) or (3S)-β-cryptoxanthin (5) is prepared by a process comprising isomerizing a compound having the Formula II:

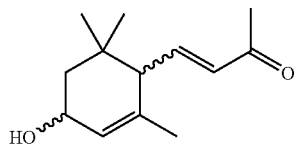

to obtain said compound having the Formula I:

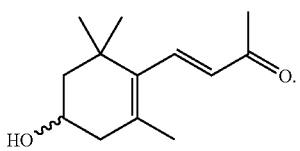

In some embodiments, (3R,3'R)-zeaxanthin (1), (3S,3'S)-zeaxanthin (2), (3R,3'S;meso)-zeaxanthin (3), (3R)-β-cryptoxanthin (4) or (3S)-β-cryptoxanthin (5) is prepared by a process comprising isomerizing a compound having the Formula II:

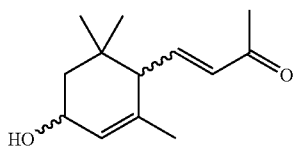

to obtain said compound having the Formula I:

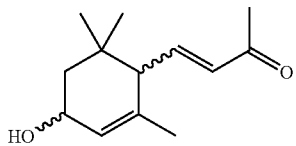

and acylating a racemic mixture of (3R)-3-hydroxy-β-ionone (8) and (3S)-3-hydroxy-β-ionone (9) using enzyme-mediated stereoselective acylation, and separating (3R)-3-acetoxy-β-ionone (14) from unesterified (3S)-3-hydroxy-β-ionone (9) using column chromatography.

DETAILED DESCRIPTION OF THE INVENTION

All chemicals and reagents were commercially available and obtained from Aldrich Chemical Co. (St. Louis, Mo.). Lipase PS (*Pseudomonas cepacia*) and lipase AK (*pseudomonas fluorescens*) were from Amano Enzyme USA (Lombard, Ill.). All carotenoids and their precursors were fully characterized by $^1$H and $^{13}$C-NMR, MS, and UV-Vis, and circular dichroism (CD). Combination of NMR and CD was employed to assign the relative and absolute stereochemistry of all synthetic carotenoids and their precursors. The purity of all compounds was determined by HPLC employing eluents A, B, C, and D.

Eluent A (hexane, 75%; $CH_2Cl_2$ 25%; MeOH, 0.5%; 0.7 mL/min) was used with a silica-based nitrile bonded column (25-cm length×4.6 mm ID; 5-μm spherical particle; Waters Corporation, Milford, Mass.). This eluent was employed to monitor the course of most reactions and determined the diastereomeric ratios of 3,6-trans-3-hydroxy-α-ionone and 3,6-cis-3-hydroxy-α-ionone. The column was protected with a Brownlee nitrile bonded guard cartridge (3-cm length×4.6 mm ID; 5-μm particle size). The column flow rate with all eluents was 0.7 mL/min and the separations were monitored at 226 nm for 3-hydroxy-α-ionone and at 286 nm for 3-hydroxy-β-ionone. The stereoisomers of zeaxanthin and β-cryptoxanthin were monitored by HPLC at 450 nm.

The optical purity of all carotenoids and their precursors was assessed by chiral HPLC on a CHIRALPAK® AD column (25-cm length×4.6 mm internal diameter) purchased from Chiral Technologies (Exton, Pa.). The column packing consisted of amylose tris-(3,5-dimethylphenylcarbamate) coated on 10 μm silica gel substrate and the column was protected with a silica gel guard cartridge (3-cm length×4.6 mm ID; 5 μm particle).

The optical purity of (3R)-3-hydroxy-β-ionone and its (3S)-enantiomer was determined by chiral HPLC with eluent B that consisted of an isocratic mixture of hexane (90%) and isobutanol (10%).

The optical purity of (3R,3'R)-zeaxanthin and its stereoisomers was monitored by eluent C. For eluent C, a two pumps system with a combination of isocratic and gradient HPLC was employed. Pump One pumped a mixture of hexane (95%) and 2-propanol (5%) and pump Two pumped a mixture of hexane (85%), and 2-propanol (15%). At time zero, 95% solvents from pump One and 5% solvents from pump Two were pumped isocratically for 10 minutes. After 10 minutes, a linear gradient was run for 15 minutes during which the solvents from pump Two were linearly increased from 5% to 40% while that of pump One were reduced from 95% to 60%. At the end of each run, the column was re-equilibrated under the original isocratic conditions for 20 minutes.

The optical purity of (3R)-β-cryptoxanthin and its (3S)-isomer was determined with eluent D that consisted of an isocratic mixture of hexane (98%) and isopropyl alcohol 2%.

The absolute configuration of (3R)-3-hydroxy-β-ionone and its (3S)-enantiomer was established by comparison of their NMR and CD spectra with those of an authentic sample of (3R)-3-hydroxy-β-ionone prepared from oxidative cleavage of naturally occurring (3R,3'R,6'R)-lutein.

Synthesis of 3-Keto-α-Ionone Ketal (17) from (rac)-α-Ionone via α-Ionone Ketal (18). The carbonyl group of (rac)-α-ionone protected was first protected with ethylene glycol in the presence of trimethylformate and catalytic amount of p-toluenesulfonic acid to afford α-ionone ketal 18 in nearly quantitative yield which was used in the following step without purification (Scheme 6). Ketal 18 was first prepared from (rac)-α-ionone by Pommer in 1958 (DE 1031301, BASF Patent, 1958).

In one embodiment of the present invention, the crude ketal 18 was oxidized with TBHP and household bleach and catalytic amounts of $K_2CO_3$ in acetonitrile at −5 to 0° C. to 3-keto-α-ionone ketal (17) in 83% isolated yield (Scheme 6). While this reaction can be carried out in other solvents such as ethyl acetate, ethylene glycol, and hexane, the highest isolated yield of 57% was obtained with acetonitrile and ethanol. This water-based oxidation system, using household laundry bleach and aqueous TBHP, has been shown to convert steroidal olefins to α,β-enones by an economical and environmentally friendly methodology (Marwah, *Green Chem.*, 2004, 6, 570-577). However, this method has not been applied to the synthesis of 3-keto-α-ionone ketal (17).

There are three reported procedures for preparation of (rac)-3-keto-α-ionone (17) in the literature. The first procedure employs tert-butyl chromate to oxidize (rac)-α-ionone to (rac)-3-keto-α-ionone in only 14% isolated yield and the second uses $Ac_2Co.4H_2O/NH_4Br/O_2$ to improve the yield to 31%. More recently, another procedure for allylic oxidation of ionone-like dienes with TBHP catalyzed by $CaCl_2$ and $MgCl_2.6H_2O$ at 60° C. has also been reported that can afford (rac)-3-keto-α-ionone in yields comparable to ours (Yang et al. *Synlett* 2006, 16: 2617-2620).

Synthesis of (rac)-3-Hydroxy-β-Ionone (8+9) from 3-Keto-α-Ionone Ketal (17) via 3-Hydroxy-α-Ionone Ketal (16) and 3-Hydroxy-α-Ionone (15). As shown in Scheme 7, ketal 18 was first reduced to (rac)-3-hydroxy-α-ionone ketal (16) which was deprotected 0.3N HCl to (rac)-3-hydroxy-α-ionone (15). The reduction of 17 to 16 was carried out with a number of reagents and after deprotection afforded 15 in 58-90% yield; the results are summarized in Table 1.

TABLE 1

Reduction of 3-keto-α-ionone ketal (17) to 3-hydroxy-α-ionone ketal (16) followed by deprotection to 3-hydroxy-α-ionone (15).

| Reducing agent | Solvent | Yield (%) of 3-Hydroxy-α-Ionone (15) | (3,6-trans:3,6-cis)-15* |
|---|---|---|---|
| NaBH$_4$ | EtOH | 58 | 1:1 |
| NaBH$_4$/dl-Tartaric acid | EtOH | 77 | 1:1 |
| NaBH$_4$-CeCl$_3$ | MeOH | 40 | 1:1.9 |
| 9-Borabicyclo[3.3.1]nonane (9-BBN) | THF | 20 | 1:1.4 |
| Sodium bis(2-methoxyethoxy)-aluminum hydride, NaAlH$_2$(OCH$_2$CH$_2$OMe)$_2$ (RED-AL ™) | TBME | 57 | 1:1 |
| Diisobutylaluminum hydride (DIBAL-H) | CH$_2$Cl$_2$ | 90 | 1:1.9 |
| Sodium tri-sec-butylborohydride, NaB[CHMeCH$_2$CH$_3$]$_3$H (N-SELECTRIDE ™) | TBME | 80 | 1:1.4 |
| Potassium tri-sec-butylborohydride KB[CHMeCH$_2$CH$_3$]$_3$H (K-SELECTRIDE ™) | TBME | 85 | 1.2:1 |

*Indicates the stereochemical relationship between the hydroxyl group at C3 and the enone side chain at C6.

Among these reducing agents, DIBAL-H, N-SELECTRIDE™, and K-SELECTRIDE™, after deprotection, produced the highest yield of 3-hydroxy-α-ionone (15). Because of the presence of two chiral centers in 15, this key intermediate is formed as a racemic mixture of four stereoisomers (two pairs of enantiomers). In one pair of enantiomers, the OH at C3 and the C6-enone side chain are trans with respect to one another and in the other pair these groups are in a cis geometry. In the following step, the base-catalyzed double bond isomerization of 15 to (rac)-3-hydroxy-β-ionone (8+9) was shown to proceed much more readily with the 3,6-trans-isomer than that with the 3,6-cis-isomer (Scheme 7).

However, the reduction of ketoketal 17 with the reagents listed in Table 1 showed no selectivity with respect to the relative stereochemistry at C3 and C6. Nonetheless, among these, K-SELECTRIDE™ provided the highest ratio of the 3,6-trans- to the 3,6-cis-isomer and was therefore selected as the reagent of choice for the reduction 3-keto-α-ionone ketal (17).

The base-catalyzed double bond isomerization of 15 to (rac)-3-hydroxy-β-ionone (8+9) was accomplished with methanolic KOH (10% wt/v) in THF at 50° C. in one hour. After column chromatography, a racemic mixture of 8 and 9 was obtained in 65% isolated yield. Therefore, in one embodiment of the present invention, (rac)-3-hydroxy-β-ionone (8+9) was synthesized from commercially available (rac)-α-ionone in 5 steps and in 46% overall yield according to the pathways shown in Schemes 6 and 7.

In 1992, Broom et al. (*Tetrahedron Lett.* 1992, 33:3197-3200) reported on the synthesis of 3-hydroxy-β-ionone from β-ionone according to the reaction pathways shown in Scheme 12.

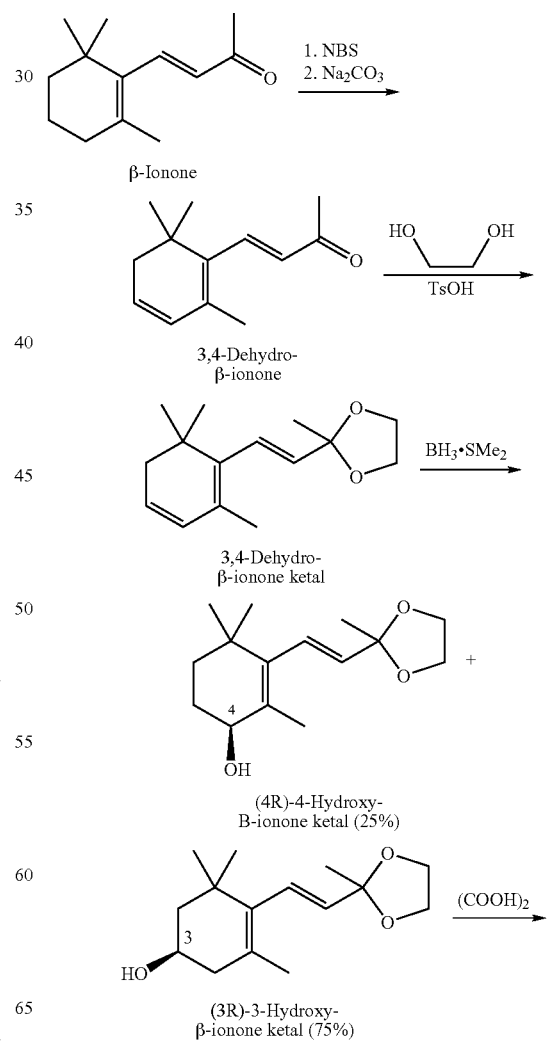

Scheme 12. Synthesis of (3R)-3-hydroxy-β-ionone according to the method of Broom et al. (*Tetrahedron Lett.* 1992, 33:3197-3200).*

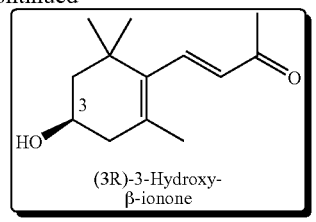

(3R)-3-Hydroxy-
β-ionone

*Carotenoid numbering system has been used.

The key starting material for this synthesis was 3,4-dehydro-β-ionone that was prepared from β-ionone according to a published procedure (Findlay & Mackay, Can. J. Chem. 1971, 49: 2369-71). This ketone was then protected as a 1,3-dioxolane to yield 3,4-dehydro-β-ionone ketal that was hydroborated with borane-dimethyl sulfide to afford a mixture of (3R)-3-hydroxy-β-ionone ketal (75%) and (4R)-4-hydroxy-β-ionone ketal (25%). (3R)-3-Hydroxy-β-ionone ketal was isolated from the mixture in 32% yield and was subsequently deprotected with oxalic acid to afford (3R)-3-hydroxy-β-ionone. Although the authors claimed that the hydroboration of 3,4-dehydro-β-ionone ketal with borane-dimethyl sulfide was stereospecific and afforded (3R)-3-hydroxy-β-ionone ketal as a single enantiomer, neither CD nor chiral HPLC data were provided to confirm the absolute configuration of the product. We have recently repeated this work and have shown that this hydroboration is not stereospecific and leads to a racemic mixture of 3-hydroxy-β-ionone. This was accomplished by analysis of the product by chiral HPLC employing eluent B. Therefore, while the method of Broom et al. provides an alternative route to (rac)-3-hydroxy-β-ionone, it fails to produce the optically active 3R or 3S stereoisomer of this hydroxyionone.

Enzyme-Mediated Acylation of (rac)-3-Hydroxy-β-Ionone (8+9). The racemic mixture of 3-hydroxy-β-ionone 8 and 9 were separated by enzyme-mediated acylation with immobilized lipase PS (pseudomonas cepacia) in EtOAc in the presence of vinyl acetate within 20 h at R.T. While (3R)-3-hydroxy-β-ionone 8 was acylated to (3R)-3-acetoxy-β-ionone (14), (3S)-3-hydroxy-β-ionone 9 remained unreacted (Scheme 8). Due to the large difference in their solubility properties, 14 and 9 were readily separated by column chromatography. Acetoxyionone 14 was nearly quantitatively hydrolyzed to hydroxyionone 8 with KOH/MeOH at 0° C. to prevent the degradation of this somewhat sensitive endgroup. According to chiral HPLC (Eluent B), (3R)-3-hydroxy-β-ionone and its (3S)-isomer were each obtained in 96% enantiomeric excess (ee). Similar results were also obtained by employing immobilized lipase AK (pseudomonas fluorescens).

Transformation of (3R)-3-Hydroxy-β-Ionone (8) and its 3S-Isomer (9) to (3R,3'R)-Zeaxanthin, (3S,3'S)-Zeaxanthin, and (3R,3'S;meso)-Zeaxanthin via Wittig Salts 12 and 13. As mentioned earlier, (3R)-3-hydroxy-β-ionone (8) and its 3S-isomer (9) were separately converted to the Wittig salts 12 and 13, respectively via vinyl-α-ionols 10 and 11 according to the reported procedure by Rüttimann and Mayer (Helv. Chim. Acta, 1980, 63:1456-62) (Scheme 9). In separate experiments, Wittig salts 12 and 13 were condensed with $C_{10}$-dialdehyde 6 according to the published procedure by Widmer et al. (Helv. Chim. Acta, 1990, 73:861-67) to afford (3R,3'R)- and (3S,3'S)-zeaxanthin, respectively (Scheme 10). Each of these stereoisomers was shown by chiral HPLC (Eluent C) to have an enantiomeric excess (ee) of 96%.

Similarly, for the synthesis of (3R,3'S;meso)-zeaxanthin (3), $C_{10}$-dialdehyde 6 was first coupled with 1 equivalent of Wittig salt 12 to yield (3R)-3-hydroxy-β-apo-12'-carotenal (19) which was further elongated to 3 with Wittig salt 13. (Scheme 10). Because these transformations have already been published, our detailed presentation of these reactions is not relevant to the present invention. However, we have carried out these experiments to simply demonstrate that (3R)-3-hydroxy-β-ionone (8) and its 3S-isomer (9) that we have prepared by a novel methodology can be applied to the synthesis of (3R,3'R)-, (3S,3'S)-, and (3R,3'S;meso)-zeaxanthin according to published procedures.

Synthesis of (3R)-β-Cryptoxanthin and (3S)-β-Cryptoxanthin. As discussed earlier, the total synthesis of (rac)-β-cryptoxanthin was first reported by Loeber et al. [J. Chem. Soc (C), 1971, 404-408] as shown in Scheme 2. Therefore, for the synthesis of the optically active (3R)-β-cryptoxanthin and its (3S)-isomer we followed the same methodology. The only exception was that we condensed optically active Wittig salts 12 and 13 in separate experiments with β-apo-12'-carotenal (20) and obtained (3R)-β-cryptoxanthin and its (3S)-enantiomer, respectively. Each of these stereoisomers was shown by chiral HPLC (Eluent D) to have an enantiomeric excess (ee) of 99%.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE 1

Preparation of (rac)-α-Ionone Ketal (18)

Freshly distilled (rac)-α-ionone (23.5 g, 110 mmol) was transferred into a 250 mL three necked flask with 10 mL hexane and was treated with ethylene glycol (18 mL, 323 mmol) and trimethylorthoformate (14 mL, 128 mmol). p-Toluenesulfonic acid (285 mg, 1.5 mmol) was added and the mixture was stirred at R.T. under nitrogen overnight. The progress of the reaction was monitored by NMR. The product was partitioned between water and hexane, and the organic layer was washed water (3×300 mL), dried over $Na_2SO_4$, and evaporated to dryness to yield a 29.7 g pale yellow oil. The product was identified by NMR as (rac)-α-Ionone Ketal (18) and was used in the next step without purification.

EXAMPLE 2

Oxidation of (rac)-α-Ionone Ketal (18) to (rac)-3-Keto-α-Ionone Ketal (17)

(rac)-α-Ionone ketal (29.7 g, from example 1) was transferred into a 1 L three-necked flask using acetonitrile (105 mL, 82.53 g, 2.0 mol). $K_2CO_3$ (1.8 g, 13 mmol) was added and the mixture was cooled down in an ice-salt bath to 0° C. under $N_2$. A 70% solution of TBHP in water (108 mL, 97.2 g 70% ≈68.0 g, 0.755 mol) was added dropwise to the mixture under $N_2$ at 0° C. in 30 min. Household bleach containing 5.25% NaOCl (356 g, 18.7 g NaOCl, 0.251 mol) was then added over a period of 8 h at −5 to 0° C. After the addition was completed, the reaction mixture was stirred at 0° C. for an additional hour. The product was treated with 2 g $NaHCO_3$ at 0° C. and then extracted with hexane (2×150 mL). The combined organic layer was washed with water (3×150 mL), dried over $Na_2SO_4$, and evaporated to dryness to give 30.3 g of pale yellow oil. The crude product was purified by column chromatography (hexane:ethyl acetate, from 98:2 to 85:15) to yield (rac)-3-keto-α-ionone ketal (17) (19.0 g, 91.0 mmol, 83%) as a pale yellow oil.

EXAMPLE 3

Reduction of (rac)-3-Keto-α-Ionone Ketal (17) with $NaBH_4$

To a solution of (rac)-3-keto-α-ionone ketal (17) (16.5 g, 66 mmol) in 100 mL ethanol was added $NaBH_4$ (3.75 g, 99 mmol) at 10° C. The mixture was kept at 10° C. and allowed to warm up to room temperature, stirred for 4 h, and the product was partitioned between water (400 mL) and ethyl acetate (150 mL). The organic layer was removed and the aqueous layer was extracted with 100 mL of ethyl acetate. The combined organic layer was washed with brine and water, dried over $Na_2SO_4$, and evaporated to dryness. The crude product (10 g) was deprotected in the following step without purification.

Deprotection of (rac)-3-hydroxy-α-ionone ketal (16). The deprotection of (rac)-3-hydroxy-α-ionone ketal (16) to (rac)-3-hydroxy-α-ionone (15) was carried out according to the following general procedure in all subsequent reduction reactions.

The crude product (10 g) was transferred into a 500 mL round bottom flask with 100 mL acetone and 20 mL water and the mixture was kept under nitrogen. The solution was treated with 16.5 mL of 0.3N HCl with dropwise addition in 10 minutes and stirred at R.T. for 3 h. The course of deprotection was monitored by NMR. The crude (rac)-3-hydroxy-α-ionone was partitioned between 300 mL water and 150 mL ethyl acetate. The organic layer was washed with saturated $NaHCO_3$, dried over $Na_2SO_4$, and evaporated to dryness to obtain 13.1 g of a yellow oil. The crude product was purified by column chromatography (hexane:acetone, from 95:5 to 85:15) to afford (rac)-3-hydroxy-α-ionone (15) (7.9 g, 38 mmol, 58%) as a yellow oil.

EXAMPLE 4

Reduction of (rac)-3-Keto-α-Ionone Ketal (17) with $NaBH_4$/dl-Tartaric Acid

A solution of dl-tartaric acid (1.8 g, 12 mmol) in ethanol (10 mL) was cooled down to 0° C. under $N_2$ and solid $NaBH_4$ (0.46 g, 12.2 mol) was added slowly in small portions. An exothermic reaction began with evolution of $H_2$. The mixture was stirred at R.T. for 20 minutes and was then cooled down to −15° C. (rac)-3-Keto-α-ionone ketal (17) (2.5 g, 10 mmol) in 8 mL ethanol was added and the mixture was stirred at −15° C. for 10 minutes. This was followed by the addition of solid $NaBH_4$ (0.23 g, 6.08 mmol) to the suspension at −15° C. The mixture was allowed to warm up to R.T. and the course of the reaction was followed by HPLC (eluent A). The product was worked up by pouring the reaction mixture into crushed ice and extraction with ethyl acetate (50 mL). The organic layer was washed with water (2×100 mL), dried over $Na_2SO_4$, and evaporated to dryness to give 2.4 g of a colorless oil identified as ketal 16. The oil was dissolved in acetone (25 mL) and water (14 mL) and treated with 1.8 mL of 0.3N HCl to deprotect the ketal as described in example 3. After work up and purification by chromatography, 1.6 g of a colorless oil was obtained that was identified as (3,6)-trans-3-hydroxy-α-ionone and (3,6)-cis-3-hydroxy-α-ionone in diastereomeric ratio of 1:1 (1.6 g, 7.7 mmol; 77%).

EXAMPLE 5

Reduction of (rac)-3-Keto-α-Ionone Ketal (17) with $NaBH_4$/Cerium Chloride

A solution of (rac)-3-keto-α-ionone ketal (17) (0.32 g, 1.28 mmol) in methanol (20 mL) was cooled down to −15° C. under $N_2$ and was treated with solid $CeCl_3$ (0.73 g, 1.96 mmol). $NaBH_4$ (80 mg, 2.11 mmol) was added at −15° C. and stirred at this temperature for 2 h. The course of the reaction was followed by HPLC (eluent A). The product was poured into a solution of $NH_4Cl$ (10%) and extracted with ethyl acetate (25 mL). The organic layer was washed with water (2×80 mL), dried over $Na_2SO_4$, and evaporated to dryness to give 0.2 g of ketal 16 as a colorless oil. The oil was dissolved in acetone (2 mL) and water (4 mL) and treated with 0.15 mL of 0.3N HCl to deprotect the ketal as described in example 3. After work up, the crude product was purified by chromatography to afford 15 (106 mg, 0.51 mmol; 40%) which was shown by HPLC (eluent A) and NMR to consist of a mixture of (3,6)-trans-3-hydroxy-α-ionone (34%) and (3,6)-cis-3-hydroxy-α-ionone (66%).

EXAMPLE 6

Reduction of (rac)-3-Keto-α-Ionone Ketal (17) with 9-BBN

A solution of (rac)-3-keto-α-ionone ketal (17) (0.2 g, 0.81 mmol) in TBME (6 mL) was cooled down to −35° C. under $N_2$ and a 2M solution of 9-BBN in THF (4 mL, 2 mmol) was added. The mixture was stirred at −40° C. for 45 min. The reaction was quenched by addition of water (1 mL) and the mixture was allowed to warm up to R.T. 3N NaOH (1.5 mL) followed by 30% $H_2O_2$ (1.5 mL) were added and the mixture was stirred for 15 min at R.T. The product was washed with water, dried over $Na_2SO_4$ and evaporated to dryness to yield ketal 16 as a colorless oil. The oil was dissolved in acetone (5 mL) and water (1.5 mL) and treated with 0.2 mL of 0.3N HCl to deprotect the ketal as described in example 3. After work up with ethyl acetate, the crude product was shown by HPLC (eluent A) to consist of a mixture of 3-keto-α-ionone (80%), (3,6)-trans-3-hydroxy-α-ionone (8.4%), and (3,6)-cis-3-hydroxy-α-ionone (11.6%).

EXAMPLE 7

Reduction of (rac)-3-Keto-α-Ionone Ketal (17) with Sodium Bis(2-Methoxyethoxy)-Aluminum Hydride (RED-AL™)

A solution of (rac)-3-keto-α-ionone ketal (17) (13.3 g, 53 mmol) in TBME (30 mL) was cooled down to −20° C. under $N_2$ and a solution of RED-AL™ in toluene (25 mL of 65 wt %, 16.84 g, 83 mmol) was added dropwise in 40 minutes. The mixture was allowed to warm up to 0° C. and stirred for 1 h at this temperature. The reaction was quenched by addition of water (10 mL) at −10° C. and stirring for 10 minutes. The product was filtered through celite using acetone. The filtrate was concentrated under reduced pressure and the residue was partitioned between TBME (120 mL) and water (300 mL). The organic layer was removed and sequentially washed with brine and water. After drying over $Na_2SO_4$ and solvent evaporation, the crude product was dissolved in acetone (50 mL) and water (20 mL) and stirred with 5 mL of 0.3 N HCl at R.T. for 2 h to deprotect the ketal 16. After work-up 10.8 g of a yellow oil was obtained. The oil was purified by column chromatography (hexane:ethyl acetate from 90:10 to 70:30) to yield (rac)-3-hydroxy-α-ionone (15) (6.27 g, 30 mmol, 57%) as a pale yellow oil which was shown by HPLC (eluent A) and NMR to consist of a 1:1 mixture of (3,6)-trans- and (3,6)-cis-3-hydroxy-α-ionone.

EXAMPLE 8

Reduction of (rac)-3-Keto-α-Ionone Ketal (17) with Diisobutylaluminum Hydride (DIBAL-H)

A solution of (rac)-3-keto-α-ionone ketal (17) (0.98 g, 3.9 mmol) in $CH_2Cl_2$ (7 mL) was cooled down to −30° C. under $N_2$ and a solution of DIBAL-H (7 mL of 1M in $CH_2Cl_2$, 7 mmol) was added with a syringe in 5 min. The mixture was stirred at −30° C. to −20° C. for 1 h. The reaction was quenched by adding water (20 mL) at −10° C. followed by 1 g of silica gel. The mixture was allowed to warm up to R.T. and stirred for 1 h. The mixture was filtered through celite and $CH_2Cl_2$ was removed under reduced pressure. The residue was dissolved in 10 mL acetone and 5 mL water and was stirred with 0.3N HCl (0.4 mL) at R.T. for 30 min. After work up with ethyl acetate and column chromatography purification, hydroxyionone 15 (0.73 g, 3.50 mmol, 90%) was shown by HPLC (eluent A) and NMR to consist of a mixture of (3,6)-trans-3-hydroxy-α-ionone (34%) and (3,6)-cis-3-hydroxy-α-ionone (66%).

EXAMPLE 9

Reduction of (rac)-3-Keto-α-Ionone Ketal (17) with Sodium Tri-sec-Butylborohydride (N-SELECTRIDE™)

A solution of (rac)-3-keto-α-ionone ketal (17) (50 mg, 0.2 mmol) in TBME (5 mL) was cooled down to −20° C. under $N_2$ and a 1M solution of N-SELECTRIDE™ in THF (0.52 mL, 0.52 mmol) diluted with TBME (1 mL) was added by a gas-tight syringe. The mixture was stirred at this temperature for 0.5 h and the product was worked up and deprotected as described in Example 3 to give 15 (33.3 mg, 0.16 mmol; 80%). This was shown by HPLC (eluent A) and NMR to consist of a mixture of (3,6)-trans-3-hydroxy-α-ionone (41%) and (3,6)-cis-3-hydroxy-α-ionone (59%).

EXAMPLE 10

Reduction of (rac)-3-Keto-α-Ionone Ketal (17) with Potassium Tri-sec-Butylborohydride (K-SELECTRIDE™)

A solution of (rac)-3-keto-α-ionone ketal (0.445 g, 1.78 mmol) in TBME (5 mL) was cooled down to −30° C. under $N_2$ and a 1M solution of K-SELECTRIDE™ in THF (2.5 mL, 2.5 mmol) was added with an air-tight syringe in 15 min. The mixture was stirred at −30° C. for 1 h and was then treated with 1.5 mL of 3 N NaOH followed by 1.5 mL of 30% $H_2O_2$. After stirring at R.T. for 30 min, the product was extracted with TBME (10 mL) and washed twice with water, dried over $Na_2SO_4$, and evaporated to dryness to give ketal 16 as a pale yellow oil. After deprotection with 0.3N HCl and purification by chromatography, the product was shown by HPLC (eluent A) and NMR to consist of a mixture of (3,6)-trans-3-hydroxy-α-ionone (55%) and (3,6)-cis-3-hydroxy-α-ionone (45%) (0.315 g, 1.51 mmol, 85%).

EXAMPLE 11

Base-Catalyzed Isomerization of 3-Hydroxy-α-Ionone (15) to (rac)-3-Hydroxy-β-Ionone (8+9)

A solution of 3-hydroxy-α-ionone (15) (1.93 g, 9.27 mmol) in THF (7 mL) was treated with 0.5 mL of a solution of KOH in methanol (10% wt./vol) under $N_2$. The mixture was heated to 50° C. for 1 h and the product was partitioned between water and ethyl acetate. The organic layer was washed with water (2×100 mL), dried with $Na_2SO_4$, and evaporated to dryness to give 1.8 g of a yellow oil. The product was purified by column chromatography (hexane: ethyl acetate, from 98:2 to 90:10) to give a yellow oil which was identified as (rac)-3-hydroxy-β-ionone (1.26 g, 6.03 mmol; 65%).

EXAMPLE 12

Enzyme-Mediated Acylation of (rac)-3-Hydroxy-β-ionone (8+9) with Lipase PS (*pseudomonas cepacia*)

To a solution of rac-3-hydroxy-α-ionone (3.26 g, 15.65 mmol) in 25 mL of ethyl acetate was added 5.0 g of immobilized lipase PS (*pseudomonas cepacia*) and vinyl acetate (1 mL, 0.934 g, 10.85 mmol). The mixture was stirred at R.T. under $N_2$ and the course of the enzymatic acylation was monitored by chiral HPLC (Eluent B, hexane:isobutanol=9/1). After 20 h the enzyme was filtered through celite and the filtrate was evaporated to dryness to give a yellow oil (4.0 g). Column chromatography (hexane:ethyl acetate, 98:2 to 80:20 of the product gave two major fractions.

The first fraction was identified from its $^1H$ NMR and UV spectrum as (3R)-3-acetoxy-β-ionone (14) (2.0 g, 7.99 mmol). This fraction was dissolved in $CH_2Cl_2$ (30 mL) and treated with KOH/MeOH (5.5 mL, 10% wt/v) for 2 hours at 0° C. The product was treated with 23 mL of 0.3N HCl to bring the pH to 5. The organic layer was sequentially washed with a saturated solution of $NaHCO_3$ (100 mL) and water (100 mL), and dried over $Na_2SO_4$. After solvent evaporation, 1.6 g of a yellow oil (7.68 mmol) was obtained which was shown by chiral HPLC (Eluent B) to be (3R)-3-hydroxy-β-ionone (8) (96% ee). A small sample of this was fully characterized from its UV, CD, $^1H$- and $^{13}C$-NMR, and mass spectra.

The second fraction (1.7 g, 8.16 mmol) was shown by chiral HPLC (Eluent B) to consist of (3S)-3-hydroxy-β-ionone (9) (96% ee). These hydroxyionones were fully characterized from their UV, CD, $^1H$- and $^{13}C$-NMR, and mass spectra.

The absolute configuration of hydroxyionones 8 and 9 was determined by comparison of their CD spectra with that of (3R)-3-hydroxy-β-ionone which was prepared by oxidative cleavage of naturally occurring (3R,3'R,6'R)-lutein.

EXAMPLE 13

Preparation of (3R)-3-Hydroxy-(β-Ionylideneethyl) triphenylphosphonium Chloride (12) From (3R)-3-Hydroxy-β-Ionone (8) Via (3R)-3-Hydroxy-Vinyl-β-Ionol (10)

A solution of (3R)-3-hydroxy-β-ionone (8) (0.852 g, 4.1 mmol) in toluene (15 mL) was cooled down to −20° C. under argon. A 1M solution of vinyl magnesium bromide (10 mL, 10 mmol) was added dropwise in 30 min and the mixture was stirred at this temperature for 1 h. The reaction was quenched with addition of 10 mL saturated ammonium chloride solution at −20° C. and stirred at R.T. for 10 min. The product was partitioned between water (100 mL) and ethyl acetate (50 mL). The organic layer was washed with water (100 mL), dried over $Na_2SO_4$, and evaporated to dryness. The crude product (0.78 g), (3R)-3-hydroxy-vinyl-β-ionol (10), was dissolved in 5 mL MeOH and directly used without purification in the next step for the preparation of the Wittig salt 12.

Triphenylphosphine hydrochloride was prepared fresh by adding 0.44 mL of concentrated HCl to triphenylphosphine (1.288 g, 4.91 mmol) in 5 mL methanol at 0° C. The salt was stirred at R.T. for 20 min and was treated with a solution of crude (3R)-3-hydroxy-vinyl-β-ionol (0.78 g) in MeOH (5 mL) by dropwise addition in 5 min at 0° C. The reaction was kept at 0° C. for 1 h and was allowed to stir to R.T. overnight. The product was partitioned between hexane (50 mL) and methanol:water=1:1 (50 mL). The aqueous layer was washed with hexane (3×50 mL) to remove the excess triphenylphosphine and the aqueous layer was extracted with $CH_2Cl_2$ (3×50 mL). The combined $CH_2Cl_2$ layer was washed with water (100 mL), dried over $Na_2SO_4$, and evaporated to dryness to give 1.4 g crude product that was crystallized from 1,2-dichloroethane (11 mL) and ethyl acetate (25 mL) at −20° C. The crystals were washed with ethyl acetate and hexane and dried under high vacuum to give (3R)-3-hydroxy-(β-ionylideneethyl)triphenyl-phosphonium chloride (12) (1.27 g, 2.46 mmol; 60%) as a grayish powder.

EXAMPLE 14

Preparation of (3S)-3-Hydroxy-(β-Ionylideneethyl) triphenylphosphonium Chloride (13) From (3S)-3-Hydroxy-β-Ionone (9) Via (3R)-3-Hydroxy-Vinyl-β-Ionol (11)

Employing the same procedure outlined in example 13, (3S)-3-hydroxy-β-ionone (9) (0.852 g, 4.1 mmol) was transformed into (3S)-3-hydroxy-(β-ionylideneethyl)triphenylphosphonium chloride (13) (1.17 g, 2.26 mmol, 55%).

EXAMPLE 15

Synthesis of (3R,3'R)-Zeaxanthin (1)

A mixture of (3R)-3-hydroxy-(β-ionylideneethyl)triphenylphosphonium chloride (12) (300 mg, 0.58 mmol), $C_{10}$-dialdehyde 6 (45.4 mg, 0.28 mmol), 1,2-epoxybutane (0.5 mL) in ethanol (5 mL) was refluxed under $N_2$ and the course of the reaction was monitored by HPLC (eluent A). After 22 h, HPLC showed the completion of the reaction. The product was filtered and the solids were washed with ethanol. Crystallization from $CH_2Cl_2$ and hexane gave a red solid that was identified from its NMR, CD, UV-Vis, and MS spectra as (3R,3'R)-zeaxanthin (1) (68 mg, 0.12 mmol, 43%). The product was shown by chiral HPLC (Eluent C) to have an enantiomeric excess (ee) of 96%.

EXAMPLE 16

Synthesis of (3S,3'S)-Zeaxanthin (2)

A mixture of (3S)-3-hydroxy-(β-ionylideneethyl)triphenylphosphonium chloride (13) (300 mg, 0.58 mmol), $C_{10}$-dialdehyde 6 (45.4 mg, 0.28 mmol), 1,2-epoxybutane (0.5 mL) in ethanol (5 mL) was refluxed under $N_2$ and the course of the reaction was monitored by HPLC (eluent A). After 22 h, HPLC showed the completion of the reaction. The product was filtered and the solids were washed with ethanol. Crystallization from $CH_2Cl_2$ and hexane gave a red solid that was identified from its NMR, CD, UV-Vis, and MS spectra as (3R,3'R)-zeaxanthin (2) (63 mg, 0.11 mmol, 39%); according to chiral HPLC (Eluent C) this product was obtained in 96% ee.

EXAMPLE 17

Synthesis of (3R,3'S;meso)-Zeaxanthin (3)

A mixture of (3R)-3-hydroxy-β-apo-12'-carotenal (19) (100 mg, 0.27 mmol), (3S)-3-hydroxy-(β-ionylideneethyl) triphenylphosphonium chloride (13) (109 mg, 0.30 mmol), 1,2-epoxybutane (0.25 mL) in ethanol (5 mL) was refluxed under $N_2$ and the course of the reaction was monitored by HPLC (eluent A). After 6 h, HPLC showed the completion of the reaction. The product was filtered and the solids were washed with ethanol. Crystallization from $CH_2Cl_2$ and hexane gave a red solid that was identified as (3R,3'S;meso)-zeaxanthin (3) (91 mg, 0.16 mmol, 59%).

EXAMPLE 18

Synthesis of (3R)-β-Cryptoxanthin (4)

A mixture of β-apo-12'-carotenal (20) (158 mg, 0.45 mmol), (3R)-3-hydroxy-(β-ionylideneethyl)triphenylphosphonium chloride (12) (269 mg, 0.52 mmol), 1,2-epoxybutane (0.39 mL) in ethanol (5 mL) was refluxed under $N_2$. After 6 h, the product was filtered and the solids were washed with ethanol. Crystallization from $CH_2Cl_2$ and hexane gave a red solid that was identified as (3R)-β-cryptoxanthin (4) (177 mg, 0.32 mmol; 70%) by comparison of its NMR, CD, and UV-Vis spectra with those of standard sample of this carotenoid. The product was shown by chiral HPLC (Eluent D) to have an optical purity of 99% (ee).

EXAMPLE 19

Synthesis of (3S)-β-Cryptoxanthin (5)

β-Apo-12'-carotenal (20) (158 mg, 0.45 mmol) was allowed to react with (3S)-3-hydroxy-(β-ionylideneethyl) triphenylphosphonium chloride (13) (269 mg, 0.52 mmol) in the presence of 1,2-epoxybutane (0.39 mL) under reflux in ethanol (5 mL). After 6 h, the product was worked up and crystallized as described in example 18 to afford (3S)-β-cryptoxanthin (5) (177 mg, 0.32 mmol; 70%). The product was shown by chiral HPLC (Eluent D) to have an optical purity of 99% (ee).

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A process for the synthesis of a compound having the Formula I:

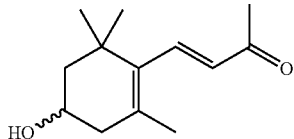

comprising isomerizing a compound having the Formula II:

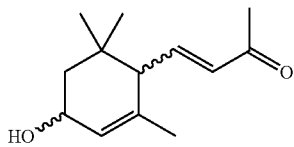

to obtain said compound having the Formula I.

2. The process of claim 1, wherein said compound having the Formula I is prepared from said compound having the Formula II by base-catalyzed double isomerization comprising reacting said compound having the Formula II with a mineral base or an organic base at a temperature ranging from 45° C. to 60° C.

3. The process of claim 2, wherein said mineral base is sodium hydroxide (NaOH) or potassium hydroxide (KOH).

4. The process of claim 1, wherein said compound having the Formula I is a racemic mixture of (rac)-3-hydroxy-β-ionone.

5. The process of claim 4, wherein said racemic mixture comprises (3R)-3-hydroxy-β-ionone (8) and (3S)-3-hydroxy-β-ionone (9) and said process further comprises enzyme-mediated stereoselective acylation of 8 and 9, and separation of (3R)-3-acetoxy-β-ionone (14) from unesterified (3S)-3-hydroxy-β-ionone (9) using column chromatography.

6. The process of claim 5, wherein said stereoselective enzyme-mediated acylation comprises acylating said racemic mixture with immobilized lipase PS (*Pseudomonas cepacia*) or lipase AK (*Pseudomonas fluorescens*) in the presence of an acyl donor to convert (3R)-3-hydroxy-β-ionone (8) to (3R)-3-acetoxy-β-ionone (14) while (3S)-3-hydroxy-β-ionone (9) remains unesterified.

7. The process of claim 6, wherein said acyl donor is vinyl acetate, vinyl benzoate or isopropenyl acetate.

8. The process of claim 6, wherein said separation comprises column chromatography on n-silica.

9. The process of claim 8, wherein said column is eluted with a combination of (1) at least one hydrocarbon solvent selected from the group consisting of pentane, hexane, heptane and cyclohexane, and (2) ethyl acetate or acetone.

10. The process of claim 9, further comprising saponifying (3R)-3-acetoxy-β-ionone (14) to obtain (3R)-3-hydroxy-β-ionone (8).

11. The process of claim 10, wherein said saponifying is with alcoholic potassium hydroxide (KOH) or sodium hydroxide (NaOH).

12. A process for separating a racemic mixture of (3R)-3-hydroxy-β-ionone (8) and (3S)-3-hydroxy-β-ionone (9) comprising acylating 8 and 9 using enzyme-mediated stereoselective acylation, and separating (3R)-3-acetoxy-β-ionone (14) from unesterified (3S)-3-hydroxy-β-ionone (9) using column chromatography.

13. The process of claim 12, wherein said enzyme-mediated stereoselective acylation comprises acylating said racemic mixture with immobilized lipase PS (*Pseudomonas cepacia*) or lipase AK (*Pseudomonas fluorescens*) in the presence of an acyl donor.

14. The process of claim 13, wherein said acyl donor is vinyl acetate, vinyl benzoate or isopropenyl acetate.

15. The process of claim 12, wherein said separation comprises column chromatography on n-silica.

16. The process of claim 15, wherein said column is eluted with a combination of (1) at least one hydrocarbon solvent selected from the group consisting of pentane, hexane, heptane and cyclohexane, and (2) ethyl acetate or acetone.

17. The process of claim 15, further comprising saponifying (3R)-3-acetoxy-β-ionone (14) to obtain (3R)-3-hydroxy-β-ionone (8).

18. The process of claim 17, wherein said saponifying is with alcoholic potassium hydroxide (KOH) or sodium hydroxide (NaOH).

19. A process for preparing (3R,3'R)-zeaxanthin (1), (3S,3'S)-zeaxanthin (2), (3R,3'S;meso)-zeaxanthin (3), (3R)-β-cryptoxanthin (4) or (3S)-β-cryptoxanthin (5) by a process comprising isomerizing a compound having the Formula II:

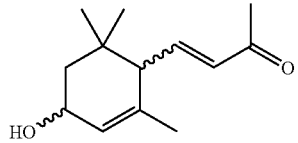

to obtain said compound having the Formula I:

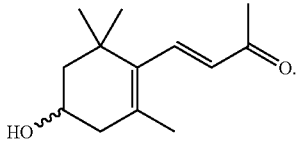

20. The process of claim 19, further comprising acylating a racemic mixture of (3R)-3-hydroxy-β-ionone (8) and (3S)-3-hydroxy-β-ionone (9) using enzyme-mediated stereoselective acylation, and separating (3R)-3-acetoxy-β-ionone (14) from unesterified (3S)-3-hydroxy-β-ionone (9) using column chromatography.

* * * * *